United States Patent
Hoveyda

(10) Patent No.: US 11,078,203 B2
(45) Date of Patent: Aug. 3, 2021

(54) DEUTERATED FEZOLINETANT

(71) Applicant: OGEDA SA, Anderlecht (BE)

(72) Inventor: Hamid Hoveyda, Brussels (BE)

(73) Assignee: Ogeda SA, Anderlecht (BE)

( * ) Notice: Subject to any disclaimer, the term of this patent is extended or adjusted under 35 U.S.C. 154(b) by 22 days.

(21) Appl. No.: 16/629,710

(22) PCT Filed: Jul. 12, 2018

(86) PCT No.: PCT/EP2018/068913
§ 371 (c)(1),
(2) Date: Jan. 9, 2020

(87) PCT Pub. No.: WO2019/012033
PCT Pub. Date: Jan. 17, 2019

(65) Prior Publication Data
US 2020/0270254 A1    Aug. 27, 2020

(30) Foreign Application Priority Data
Jul. 12, 2017   (EP) ..................................... 17180908

(51) Int. Cl.
| C07D 487/04 | (2006.01) |
| A61P 5/08 | (2006.01) |
| A61P 5/24 | (2006.01) |

(52) U.S. Cl.
CPC .............. *C07D 487/04* (2013.01); *A61P 5/08* (2018.01); *A61P 5/24* (2018.01); *C07B 2200/05* (2013.01)

(58) Field of Classification Search
CPC . C07D 487/04; A61P 5/08; A61P 5/24; C07B 2200/05
See application file for complete search history.

(56) References Cited

U.S. PATENT DOCUMENTS

2015/0232471 A1* 8/2015 Hoveyda ................. A61P 11/14
514/249

FOREIGN PATENT DOCUMENTS

WO        2014/154895 A1    10/2014

OTHER PUBLICATIONS

International Search Report dated Sep. 19, 2018 and Written Opinion in corresponding International application No. PCT/EP2018/068913; 9 pages.
Fisher Michael B et al., "The complexities inherent in attempts to decrease drug clearance by blocking sites of CYP-mediated metabolism", Current Opinion in Drug Discovery and Develop, Current Drugs, London, GB, vol. 9, No. 1, Jan. 1, 2006, pp. 101-109, 9 pgs.
Adeppa et al., "Improved Method for the Preparation of 1,1-Dimethyl-3-arylureas Using Chlorocarbonylsulfenyl Chloride", Synth Commun., 2012, vol. 42, pp. 714-721, 9 pgs.
Fraser et al., "The NK3 Receptor Antagonist ESN364 Interrupts Pulsatile LH Secretion and Moderates Levels of Ovarian Hormones Throughout the Menstrual Cycle", Endocrinol., 2015, vol. 156, pp. 4214-4225, 12 pgs.
Struthers et al., "Pharmacological Characterization of a Novel Nonpeptide Antagonist of the Human Gonadotropin-Releasing Hormone Receptor, NBI-42902", Endocrinol., 2007, vol. 148, pp. 857-867, 11 pgs.
Wickings et al., "Determination of biologically active LH in the serum of male rhesus monkeys (*Macaca mulatta*)", J. Reprod. Fert., 1979, vol. 57, pp. 497-504, 8 pgs.

\* cited by examiner

*Primary Examiner* — Timothy R Rozof
(74) *Attorney, Agent, or Firm* — McCarter & English, LLP; Maria Laccotripe Zacharakis; Xin Zhang

(57) ABSTRACT

Deuterated fezolinetant (R)-(4-fluorophenyl)-(8-methyl-3-(3-(methyl-d3)-1,2,4-thiadiazol-5-yl)-5,6-dihydro-[1,2,4]triazolo[4,3-a]pyrazin-7(8H)-yl)methanone:

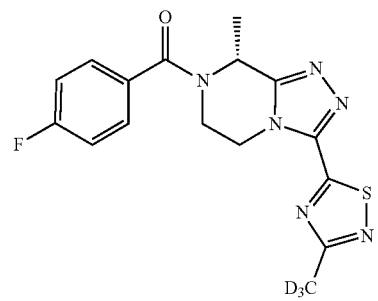

or a pharmaceutically acceptable salt or solvate thereof, as an NK-3 antagonist. Also, methods of modulating NK-3 receptor activity including administering an effective amount of the compound or pharmaceutically acceptable salt or solvate thereof. Additionally, a process for manufacturing the compound or pharmaceutically acceptable salt or solvate thereof.

9 Claims, 1 Drawing Sheet

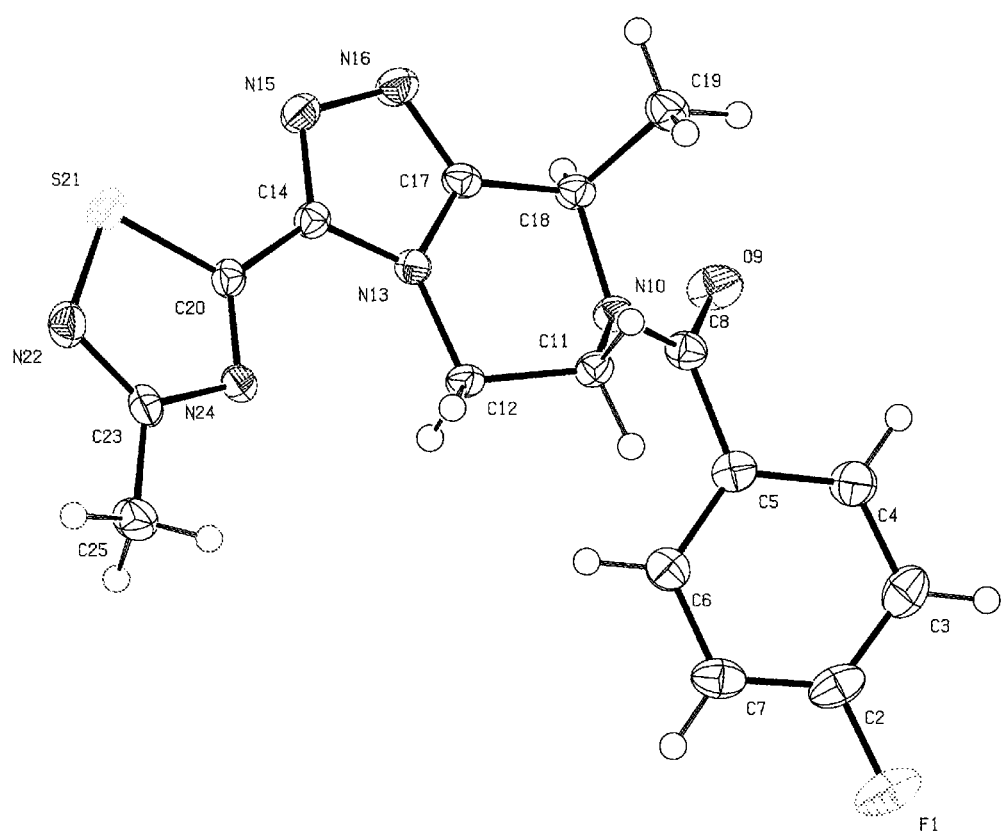

DEUTERATED FEZOLINETANT

FIELD

The present invention relates to deuterated fezolinetant, including pharmaceutically acceptable salts and solvates thereof, as selective antagonist of neurokinin-3 (NK-3) receptor and useful as therapeutic compound, particularly in the treatment and/or prevention of sex-hormone dependent diseases.

BACKGROUND

Fezolinetant was developed as selective antagonist of NK-3 receptor and is useful as therapeutic compound, particularly in the treatment and/or prevention of sex-hormone dependent diseases. Fezolinetant corresponds to (R)-(4-fluorophenyl)-(8-methyl-3-(3-methyl-1,2,4-thiadiazol-5-yl)-5,6-dihydro-[1,2,4]trizolo[4,3-a]pyrazin-7(8H)-yl) methanone and is described in WO2014/154895.

Drug-drug interactions are the most common type of drug interactions. They can decrease how well the medications works, may cause serious unexpected side effects, or even increase the blood level and possible toxicity of a certain drug.

Drug interaction may occur by pharmacokinetic interaction, during which one drug affects another drug's absorption, distribution, metabolism, or excretion. Regarding metabolism, it should be noted that drugs are usually eliminated from the body as either the unchanged drug or as a metabolite. Enzymes in the liver, usually the cytochrome P450s (CYPs) enzymes, are often responsible for metabolizing drugs. Therefore, determining the CYP profile of a drug is of high relevancy to determine if it will affect the activity of CYPs and thus if it may lead to drug-drug interactions.

The five most relevant CYPs for drug-drug interaction are CYP3A4, 2C9, 2C19, 1A2 and 2D6, among which isoforms 3A4, 2C9 and 2C19 are the major ones. The less a drug inhibits these CYPs, the less drug-drug interactions would be expected.

Therefore, it is important to provide drugs that present the safest CYP profile in order to minimize as much as possible the potential risks of drug-drug interactions.

Even if fezolinetant possesses a good CYP profile, providing analogs of fezolinetant with a further improved CYP profile would be valuable for patients.

In a completely unexpected way, the Applicant evidenced that deuteration of fezolinetant provides a further improved CYP profile, especially on isoforms CYP 2C9 and 2C19. This was evidenced for the deuterated form (R)-(4-fluorophenyl)-(8-methyl-3-(3-(methyl-d3)-1,2,4-thiadiazol-5-yl)-5,6-dihydro-[1,2,4]trizolo[4,3-a]pyrazin-7(8H)-yl)methanone, hereafter referred to as "deuterated fezolinetant".

Importantly, deuterated fezolinetant retains the biological activity of fezolinetant as well as its lipophilic efficiency.

Deuterated fezolinetant also presents the advantage to enable improvement of the in vivo half-life of the drug. For example, half-life is increased by a factor 2 in castrated monkeys, compared to fezolinetant.

The invention thus encompasses (R)-(4-fluorophenyl)-(8-methyl-3-(3-(methyl-d3)-1,2,4-thiadiazol-5-yl)-5,6-dihydro-[1,2,4]trizolo[4,3-a]pyrazin-7(8H)-yl)methanone and pharmaceutically acceptable salts and solvates thereof, as well as methods of use of this compound as antagonist to the NK-3 receptor.

SUMMARY

The invention thus relates to (R)-(4-fluorophenyl)-(8-methyl-3-(3-(methyl-d3)-1,2,4-thiadiazol-5-yl)-5,6-dihydro-[1,2,4]trizolo[4,3-a]pyrazin-7(8H)-yl)methanone or a pharmaceutically acceptable salt or solvate thereof.

It also provides a pharmaceutical composition comprising (R)-(4-fluorophenyl)-(8-methyl-3-(3-(methyl-d3)-1,2,4-thiadiazol-5-yl)-5,6-dihydro-[1,2,4]trizolo[4,3-a]pyrazin-7 (8H)-yl)methanone or a pharmaceutically acceptable salt or solvate thereof, and at least one pharmaceutically acceptable carrier, diluent, excipient and/or adjuvant.

The invention further relates to a medicament comprising ((R)-(4-fluorophenyl)-(8-methyl-3-(3-(methyl-d3)-1,2,4-thiadiazol-5-yl)-5,6-dihydro-[1,2,4]trizolo[4,3-a]pyrazin-7 (8H)-yl)methanone or a pharmaceutically acceptable salt or solvate thereof.

The invention also relates to (R)-(4-fluorophenyl)-(8-methyl-3-(3-(methyl-d3)-1,2,4-thiadiazol-5-yl)-5,6-dihydro-[1,2,4]trizolo[4,3-a]pyrazin-7(8H)-yl)methanone or a pharmaceutically acceptable salt or solvate thereof for use in treating and/or preventing depression, anxiety, psychosis, schizophrenia, psychotic disorders, bipolar disorders, cognitive disorders, Parkinson's disease, Alzheimer's disease, attention deficit hyperactivity disorder (ADHD), pain, convulsion, obesity, inflammatory diseases including irritable bowel syndrome (IBS) and inflammatory bowel disorders, emesis, pre-eclampsia, airway related diseases including chronic obstructive pulmonary disease, asthma, airway hyperresponsiveness, bronchoconstriction and cough, urinary incontinence, reproduction disorders, contraception and sex hormone-dependent diseases including but not limited to benign prostatic hyperplasia (BPH), prostatic hyperplasia, metastatic prostatic carcinoma, testicular cancer, breast cancer, ovarian cancer, androgen dependent acne, male pattern baldness, endometriosis, abnormal puberty, uterine fibrosis, uterine fibroid tumor, uterine leiomyoma, hormone-dependent cancers, hyperandrogenism, hirsutism, virilization, polycystic ovary syndrome (PCOS), premenstrual dysphoric disease (PMDD), HAIR-AN syndrome (hyperandrogenism, insulin resistance and acanthosis *nigricans*), ovarian hyperthecosis (HAIR-AN with hyperplasia of luteinized theca cells in ovarian stroma), other manifestations of high intraovarian androgen concentrations (e.g. follicular maturation arrest, atresia, anovulation, dysmenorrhea, dysfunctional uterine bleeding, infertility), androgen-producing tumor (virilizing ovarian tumor or virilizing adrenal tumor), menorrhagia and adenomyosis.

Another object of the invention is (R)-(4-fluorophenyl)-(8-methyl-3-(3-(methyl-d3)-1,2,4-thiadiazol-5-yl)-5,6-dihydro-[1,2,4]trizolo[4,3-a]pyrazin-7(8H)-yl)methanone or a pharmaceutically acceptable salt or solvate thereof for use in treating and/or preventing hot flashes.

A further object of the invention is (R)-(4-fluorophenyl)-(8-methyl-3-(3-(methyl-d3)-1,2,4-thiadiazol-5-yl)-5,6-dihydro-[1,2,4]trizolo[4,3-a]pyrazin-7(8H)-yl)methanone or a pharmaceutically acceptable salt or solvate thereof for use as a lowering agent of the circulating LH levels.

The invention also provides a process of manufacturing (R)-(4-fluorophenyl)-(8-methyl-3-(3-(methyl-d3)-1,2,4-thiadiazol-5-yl)-5,6-dihydro-[1,2,4]trizolo[4,3-a]pyrazin-7 (8H)-yl)methanone or a pharmaceutically acceptable salt or solvate thereof, as described below.

The invention also relates to intermediate compound of Formula (ii) described below.

BRIEF DESCRIPTION OF THE DRAWING

FIG. 1 is an X-ray crystal structure of deuterated fezolinetant with thermal displacement ellipsoids drawn at the 50% probability level.

DETAILED DESCRIPTION

As noted above, the invention relates to (R)-(4-fluorophenyl)-(8-methyl-3-(3-(methyl-d3)-1,2,4-thiadiazol-5-yl)-5,6-dihydro-[1,2,4]trizolo[4,3-a]pyrazin-7(8H)-yl)methanone (also referred to hereafter as "deuterated fezolinetant"):

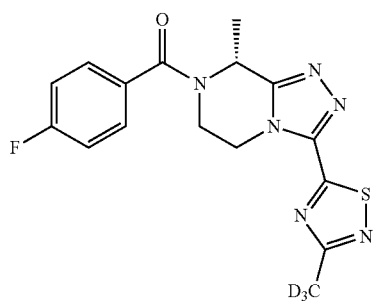 [SMILES: [2H]C([2H])([2H])c1nsc(-c2nnc3n2CCN(C(=O)c2ccc(F)cc2)[C@@H]3C)n1]

or a pharmaceutically acceptable salt or solvate thereof.

Deuterated fezolinetant can be prepared by different ways with reactions known to a person skilled in the art.

The invention also relates to a process of manufacturing of deuterated fezolinetant, comprising the following steps:

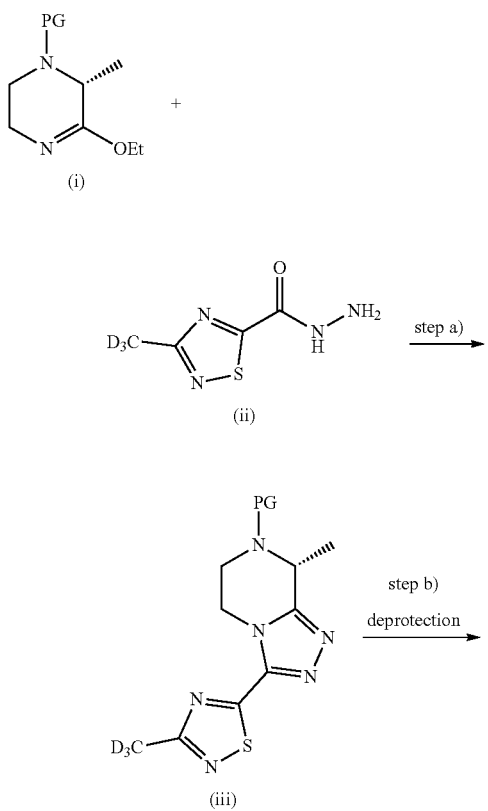

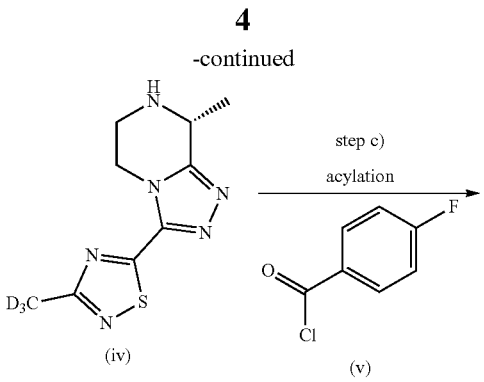

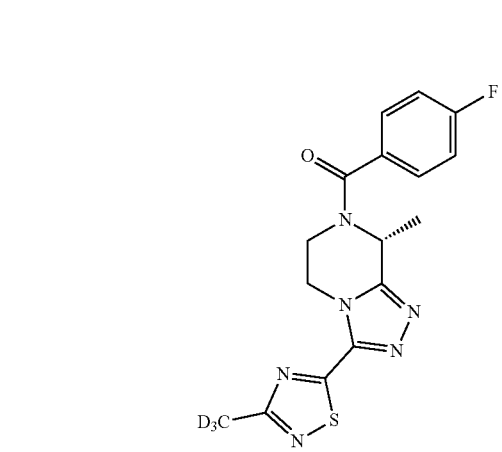

The process of the invention is thus characterized in that it comprises the following steps:

a) reacting a compound of Formula (i)

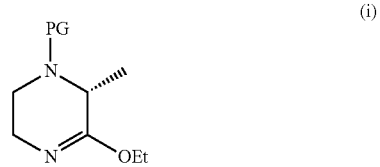

wherein:

PG represents a suitable protecting group such as for example 2,4-dimethoxybenzyl (DMB), 4-methoxybenzyl (PMB), tert-butoxycarbonyl (Boc), allyl, diphenyl-phosphiramide (DPP), 2-trimethylsilylethanesulfonyl (SES), preferably PG is DMB;

with a compound of Formula (ii)

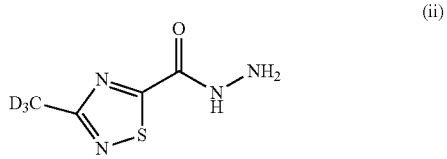 [SMILES: [2H]C([2H])([2H])c1nsc(C(=O)NN)n1]

so as to obtain a compound of Formula (iii)

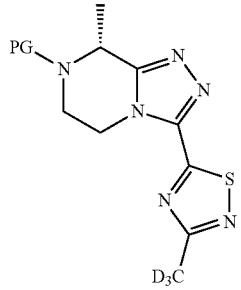

(iii)

wherein PG is as defined above;

b) deprotection of compound of Formula (iii) with a suitable deprotection agent to afford compound of Formula (iv)

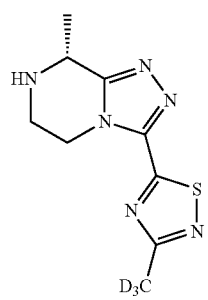

(iv)

c) N-acylation of compound of Formula (iv), with a compound of Formula (v)

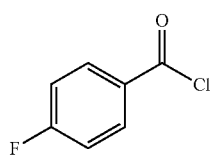

(v)

leading to deuterated fezolinetant.

In a preferred embodiment, the protecting group PG used in the process of the invention is DMB. In such case, a preferred suitable deprotection agent is trifluoroacetic acid (TFA).

According to one embodiment, intermediate of Formula (ii) can be prepared according to the following route of synthesis:

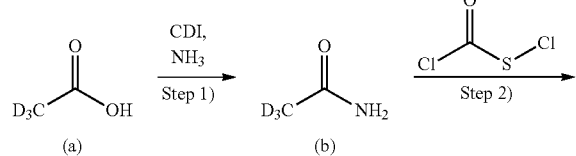

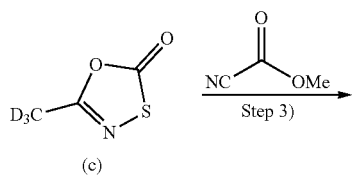

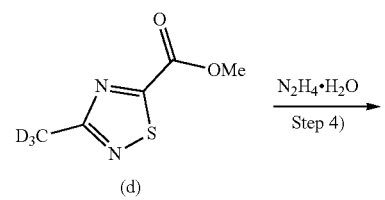

The invention thus also relates to a process for the manufacturing of intermediate of Formula (II), comprising:

1) activating d3-acetic acid of Formula (a)

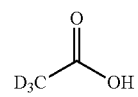

(a)

with N, N'-carbonyldiimidazole (CDI) to form the activated ester followed by the formation of the corresponding d₃-acetamide of Formula (b) by treatment with ammonia:

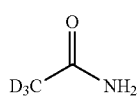

(b)

2) ring closure on d3-acetamide of Formula (b) in presence of chlorocarbonyl sulfonyl chloride leading to compound of Formula (c)

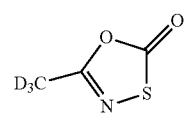

(c)

3) reacting compound of Formula (c) in presence of methyl cyanoformate leading to compound of Formula (d)

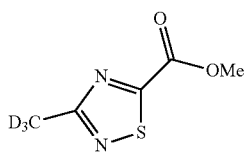

(d)

4) reacting compound of Formula (d) in presence of hydrazine hydrate to form intermediate of Formula (ii).

Reaction schemes as described in the example section are illustrative only and should not be construed as deuterated fezolinetant can be prepared only using the synthesis of the invention detailed in the examples below.

The invention is further directed to the use of deuterated fezolinetant or a pharmaceutically acceptable salt or solvate thereof as antagonist to the NK-3 receptor.

Accordingly, in another aspect, the invention relates to the use of deuterated fezolinetant or a pharmaceutically acceptable salt or solvate thereof for the synthesis of a pharmaceutical active ingredients, such as selective NK-3 receptor antagonists.

Deuterated fezolinetant is therefore useful as medicament, in particular in the prevention and/or treatment of depression, anxiety, psychosis, schizophrenia, psychotic disorders, bipolar disorders, cognitive disorders, Parkinson's disease, Alzheimer's disease, attention deficit hyperactivity disorder (ADHD), pain, convulsion, obesity, inflammatory diseases including irritable bowel syndrome (IBS) and inflammatory bowel disorders, emesis, pre-eclampsia, airway related diseases including chronic obstructive pulmonary disease, asthma, airway hyperresponsiveness, bronchoconstriction and cough, urinary incontinence, reproduction disorders, contraception and sex hormone-dependent diseases including but not limited to benign prostatic hyperplasia (BPH), prostatic hyperplasia, metastatic prostatic carcinoma, testicular cancer, breast cancer, ovarian cancer, androgen dependent acne, male pattern baldness, endometriosis, abnormal puberty, uterine fibrosis, uterine fibroid tumor, uterine leiomyoma, hormone-dependent cancers, hyperandrogenism, hirsutism, virilization, polycystic ovary syndrome (PCOS), premenstrual dysphoric disease (PMDD), HAIR-AN syndrome (hyperandrogenism, insulin resistance and acanthosis *nigricans*), ovarian hyperthecosis (HAIR-AN with hyperplasia of luteinized theca cells in ovarian stroma), other manifestations of high intraovarian androgen concentrations (e.g. follicular maturation arrest, atresia, anovulation, dysmenorrhea, dysfunctional uterine bleeding, infertility), androgen-producing tumor (virilizing ovarian tumor or virilizing adrenal tumor), menorrhagia and adenomyosis.

The invention also provides for a method for delaying in patient the onset of depression, anxiety, psychosis, schizophrenia, psychotic disorders, bipolar disorders, cognitive disorders, Parkinson's disease, Alzheimer's disease, attention deficit hyperactivity disorder (ADHD), pain, convulsion, obesity, inflammatory diseases including irritable bowel syndrome (IBS) and inflammatory bowel disorders, emesis, pre-eclampsia, airway related diseases including chronic obstructive pulmonary disease, asthma, airway hyperresponsiveness, bronchoconstriction and cough, urinary incontinence, reproduction disorders, contraception and sex hormone-dependent diseases including but not limited to benign prostatic hyperplasia (BPH), prostatic hyperplasia, metastatic prostatic carcinoma, testicular cancer, breast cancer, ovarian cancer, androgen dependent acne, male pattern baldness, endometriosis, abnormal puberty, uterine fibrosis, uterine fibroid tumor, uterine leiomyoma, hormone-dependent cancers, hyperandrogenism, hirsutism, virilization, polycystic ovary syndrome (PCOS), premenstrual dysphoric disease (PMDD), HAIR-AN syndrome (hyperandrogenism, insulin resistance and acanthosis *nigricans*), ovarian hyperthecosis (HAIR-AN with hyperplasia of luteinized theca cells in ovarian stroma), other manifestations of high intraovarian androgen concentrations (e.g. follicular maturation arrest, atresia, anovulation, dysmenorrhea, dysfunctional uterine bleeding, infertility), androgen-producing tumor (virilizing ovarian tumor or virilizing adrenal tumor), menorrhagia and adenomyosis comprising the administration of a pharmaceutically effective amount of deuterated fezolinetant or a pharmaceutically acceptable salt or solvate thereof to a patient in need thereof.

Deuterated fezolinetant is especially useful in the treatment and/or prevention of sex hormone-dependent diseases including but not limited to benign prostatic hyperplasia (BPH), prostatic hyperplasia, metastatic prostatic carcinoma, testicular cancer, breast cancer, ovarian cancer, androgen dependent acne, male pattern baldness, endometriosis, abnormal puberty, uterine fibrosis, uterine fibroid tumor, uterine leiomyoma, hormone-dependent cancers, hyperandrogenism, hirsutism, virilization, polycystic ovary syndrome (PCOS), premenstrual dysphoric disease (PMDD), HAIR-AN syndrome (hyperandrogenism, insulin resistance and acanthosis *nigricans*), ovarian hyperthecosis (HAIR-AN with hyperplasia of luteinized theca cells in ovarian stroma), other manifestations of high intraovarian androgen concentrations (e.g. follicular maturation arrest, atresia, anovulation, dysmenorrhea, dysfunctional uterine bleeding, infertility), androgen-producing tumor (virilizing ovarian tumor or virilizing adrenal tumor), menorrhagia and adenomyosis.

In a specific embodiment, deuterated fezolinetant is especially useful in the treatment and/or prevention of benign prostatic hyperplasia (BPH), endometriosis, uterine fibrosis, uterine fibroid tumor, uterine leiomyoma, polycystic ovary syndrome (PCOS), premenstrual dysphoric disease (PMDD), HAIR-AN syndrome (hyperandrogenism, insulin resistance and acanthosis *nigricans*), ovarian hyperthecosis (HAIR-AN with hyperplasia of luteinized theca cells in ovarian stroma), other manifestations of high intraovarian androgen concentrations (e.g. follicular maturation arrest, atresia, anovulation, dysmenorrhea, dysfunctional uterine bleeding, infertility), androgen-producing tumor (virilizing ovarian tumor or virilizing adrenal tumor), menorrhagia and adenomyosis.

In a specific embodiment, deuterated fezolinetant is especially useful in the treatment and/or prevention of endometriosis, uterine fibrosis, uterine fibroid tumor, uterine leiomyoma, polycystic ovary syndrome (PCOS) and benign prostatic hyperplasia (BPH).

In a specific embodiment, deuterated fezolinetant is especially useful in the treatment and/or prevention of endometriosis. In a specific embodiment, deuterated fezolinetant is especially useful in the treatment and/or prevention of uterine fibrosis. In a specific embodiment, deuterated fezolinetant is especially useful in the treatment and/or prevention of uterine fibroid tumor. In a specific embodiment, deuterated fezolinetant is especially useful in the treatment and/or prevention of uterine leiomyoma. In a specific embodiment, deuterated fezolinetant is especially useful in the treatment and/or prevention of polycystic ovary syndrome (PCOS). In a specific embodiment, deuterated fezolinetant is especially useful in the treatment and/or prevention of benign prostatic hyperplasia (BPH).

In a specific embodiment, deuterated fezolinetant is especially useful in the treatment and/or prevention of hot flashes also known as hot flushes.

The invention also provides for a method for delaying in patient the onset of hot flashes, comprising the administration of a pharmaceutically effective amount of deuterated fezolinetant or a pharmaceutically acceptable salt or solvate thereof to a patient in need thereof.

In a specific embodiment, deuterated fezolinetant is especially useful in the treatment and/or prevention of peri-menopausal conditions (i.e. 'hot flashes'), in vitro fertilization ('IVF'), male contraceptive, female contraceptive, castration of sex offenders.

In a specific embodiment, deuterated fezolinetant is especially useful in the treatment and/or prevention of hot flashes related to peri-menopausal conditions, menopausal conditions and/or postmenopausal conditions.

In a specific embodiment, deuterated fezolinetant is especially useful in the treatment and/or prevention of hot flashes which are a consequence of hormone therapy intentionally lowering the level of sex hormones, such as for example therapy-induced hot flashes in breast, uterine or prostate cancers.

Deuterated fezolinetant is also useful in the treatment of gynecological disorders and infertility. In particular, the invention provides methods to lower and/or suppress the LH-surge in assisted conception.

Deuterated fezolinetant is also useful to cause male castration and to inhibit the sex drive in men. This is of particular interest in the treatment of male sexual offenders.

The invention further provides the use of deuterated fezolinetant or a pharmaceutically acceptable salt or solvate thereof for the manufacture of a medicament for treating and/or preventing depression, anxiety, psychosis, schizophrenia, psychotic disorders, bipolar disorders, cognitive disorders, Parkinson's disease, Alzheimer's disease, attention deficit hyperactivity disorder (ADHD), pain, convulsion, obesity, inflammatory diseases including irritable bowel syndrome (IBS) and inflammatory bowel disorders, emesis, pre-eclampsia, airway related diseases including chronic obstructive pulmonary disease, asthma, airway hyperresponsiveness, bronchoconstriction and cough, urinary incontinence, reproduction disorders, contraception and sex hormone-dependent diseases including but not limited to benign prostatic hyperplasia (BPH), prostatic hyperplasia, metastatic prostatic carcinoma, testicular cancer, breast cancer, ovarian cancer, androgen dependent acne, male pattern baldness, endometriosis, abnormal puberty, uterine fibrosis, uterine fibroid tumor, uterine leiomyoma, hormone-dependent cancers, hyperandrogenism, hirsutism, virilization, polycystic ovary syndrome (PCOS), premenstrual dysphoric disease (PMDD), HAIR-AN syndrome (hyperandrogenism, insulin resistance and acanthosis *nigricans*), ovarian hyperthecosis (HAIR-AN with hyperplasia of luteinized theca cells in ovarian stroma), other manifestations of high intraovarian androgen concentrations (e.g. follicular maturation arrest, atresia, anovulation, dysmenorrhea, dysfunctional uterine bleeding, infertility), androgen-producing tumor (virilizing ovarian tumor or virilizing adrenal tumor), menorrhagia and adenomyosis in a patient.

The invention especially provides the use of deuterated fezolinetant a pharmaceutically acceptable salt or solvate thereof for the manufacture of a medicament to treat and/or prevent sex hormone-dependent diseases including but not limited to benign prostatic hyperplasia (BPH), prostatic hyperplasia, metastatic prostatic carcinoma, testicular cancer, breast cancer, ovarian cancer, androgen dependent acne, male pattern baldness, endometriosis, abnormal puberty, uterine fibrosis, uterine fibroid tumor, uterine leiomyoma, hormone-dependent cancers, hyperandrogenism, hirsutism, virilization, polycystic ovary syndrome (PCOS), premenstrual dysphoric disease (PMDD), HAIR-AN syndrome (hyperandrogenism, insulin resistance and acanthosis *nigricans*), ovarian hyperthecosis (HAIR-AN with hyperplasia of luteinized theca cells in ovarian stroma), other manifestations of high intraovarian androgen concentrations (e.g. follicular maturation arrest, atresia, anovulation, dysmenorrhea, dysfunctional uterine bleeding, infertility), androgen-producing tumor (virilizing ovarian tumor or virilizing adrenal tumor), menorrhagia and adenomyosis.

In a specific embodiment, deuterated fezolinetant or a pharmaceutically acceptable salt or solvate thereof may be used for the manufacture of a medicament to treat and/or prevent endometriosis, uterine fibrosis, uterine fibroid tumor, uterine leiomyoma, polycystic ovary syndrome (PCOS) and benign prostatic hyperplasia (BPH).

In a specific embodiment, deuterated fezolinetant or a pharmaceutically acceptable salt or solvate thereof may be used for the manufacture of a medicament to treat and/or prevent endometriosis. In a specific embodiment, deuterated fezolinetant or a pharmaceutically acceptable salt or solvate thereof may be used for the manufacture of a medicament to treat and/or prevent uterine fibrosis. In a specific embodiment, deuterated fezolinetant or a pharmaceutically acceptable salt or solvate thereof may be used for the manufacture of a medicament to treat and/or prevent uterine fibroid tumor. In a specific embodiment, deuterated fezolinetant or a pharmaceutically acceptable salt or solvate thereof may be used for the manufacture of a medicament to treat and/or prevent uterine leiomyoma. In a specific embodiment, deuterated fezolinetant or a pharmaceutically acceptable salt or solvate thereof may be used for the manufacture of a medicament to treat and/or prevent polycystic ovary syndrome (PCOS). In a specific embodiment, deuterated fezolinetant or a pharmaceutically acceptable salt or solvate thereof may be used for the manufacture of a medicament to treat and/or prevent benign prostatic hyperplasia (BPH).

In a specific embodiment, deuterated fezolinetant or a pharmaceutically acceptable salt or solvate thereof may be used for the manufacture of a medicament to treat and/or prevent hot flashes.

In a specific embodiment, deuterated fezolinetant or a pharmaceutically acceptable salt or solvate thereof may be used for the manufacture of a medicament to treat and/or prevent peri-menopausal conditions (i.e. 'hot flashes'), in vitro fertilization ('IVF'), male contraceptive, female contraceptive, castration of sex offenders.

In a specific embodiment, deuterated fezolinetant or a pharmaceutically acceptable salt or solvate thereof may be used for the manufacture of a medicament to treat and/or prevent hot flashes related to peri-menopausal conditions, menopausal conditions and/or postmenopausal conditions.

In a specific embodiment, deuterated fezolinetant or a pharmaceutically acceptable salt or solvate thereof may be used for the manufacture of a medicament to treat and/or prevent hot flashes which are a consequence of hormone therapy intentionally lowering the level of sex hormones, such as for example therapy-induced hot flashes in breast, uterine or prostate cancers.

The invention further provides the use of deuterated fezolinetant or a pharmaceutically acceptable salt or solvate thereof for the manufacture of a medicament to lower and/or suppress the LH-surge in assisted conception in a patient. Preferably the patient is a warm-blooded animal, more preferably a woman.

The invention further provides the use of deuterated fezolinetant or a pharmaceutically acceptable salt or solvate thereof for the manufacture of a medicament to cause male castration and to inhibit the sex drive in men. This is of particular interest in the treatment of male sexual offenders.

The invention further provides a method for treating and/or preventing depression, anxiety, psychosis, schizophrenia, psychotic disorders, bipolar disorders, cognitive disorders, Parkinson's disease, Alzheimer's disease, attention deficit hyperactivity disorder (ADHD), pain, convulsion, obesity, inflammatory diseases including irritable bowel syndrome (IBS) and inflammatory bowel disorders, emesis, pre-eclampsia, airway related diseases including chronic obstructive pulmonary disease, asthma, airway hyperresponsiveness, bronchoconstriction and cough, urinary incontinence, reproduction disorders, contraception and sex hormone-dependent diseases including but not limited to benign prostatic hyperplasia (BPH), prostatic hyperplasia, metastatic prostatic carcinoma, testicular cancer, breast cancer, ovarian cancer, androgen dependent acne, male pattern baldness, endometriosis, abnormal puberty, uterine fibrosis, uterine fibroid tumor, uterine leiomyoma, hormone-dependent cancers, hyperandrogenism, hirsutism, virilization, polycystic ovary syndrome (PCOS), premenstrual dysphoric disease (PMDD), HAIR-AN syndrome (hyperandrogenism, insulin resistance and acanthosis *nigricans*), ovarian hyperthecosis (HAIR-AN with hyperplasia of luteinized theca cells in ovarian stroma), other manifestations of high intraovarian androgen concentrations (e.g. follicular maturation arrest, atresia, anovulation, dysmenorrhea, dysfunctional uterine bleeding, infertility), androgen-producing tumor (virilizing ovarian tumor or virilizing adrenal tumor), menorrhagia and adenomyosis, comprising administering an effective amount of deuterated fezolinetant or a pharmaceutically acceptable salt or solvate thereof, to a patient in need thereof.

The invention especially provides a method for treating and/or preventing sex hormone-dependent diseases including but not limited to benign prostatic hyperplasia (BPH), prostatic hyperplasia, metastatic prostatic carcinoma, testicular cancer, breast cancer, ovarian cancer, androgen dependent acne, male pattern baldness, endometriosis, abnormal puberty, uterine fibrosis, uterine fibroid tumor, uterine leiomyoma, hormone-dependent cancers, hyperandrogenism, hirsutism, virilization, polycystic ovary syndrome (PCOS), premenstrual dysphoric disease (PMDD), HAIR-AN syndrome (hyperandrogenism, insulin resistance and acanthosis *nigricans*), ovarian hyperthecosis (HAIR-AN with hyperplasia of luteinized theca cells in ovarian stroma), other manifestations of high intraovarian androgen concentrations (e.g. follicular maturation arrest, atresia, anovulation, dysmenorrhea, dysfunctional uterine bleeding, infertility), androgen-producing tumor (virilizing ovarian tumor or virilizing adrenal tumor), menorrhagia and adenomyosis, comprising administering an effective amount of deuterated fezolinetant or a pharmaceutically acceptable salt or solvate thereof, to a patient in need thereof.

In a specific embodiment, the method of the invention is for treating and/or preventing endometriosis, uterine fibrosis, uterine fibroid tumor, uterine leiomyoma, polycystic ovary syndrome (PCOS) and benign prostatic hyperplasia (BPH).

In a specific embodiment, the method of the invention is for treating and/or preventing endometriosis. In a specific embodiment, the method of the invention is for treating and/or preventing uterine fibrosis. In a specific embodiment, the method of the invention is for treating and/or preventing uterine fibroid tumor. In a specific embodiment, the method of the invention is for treating and/or preventing uterine leiomyoma. In a specific embodiment, the method of the invention is for treating and/or preventing polycystic ovary syndrome (PCOS). In a specific embodiment, the method of the invention is for treating and/or preventing benign prostatic hyperplasia (BPH).

In a specific embodiment, the method of the invention is for treating and/or preventing hot flashes.

In a specific embodiment, the method of the invention is for treating and/or preventing peri-menopausal conditions (i.e. 'hot flashes'), in vitro fertilization ('IVF'), male contraceptive, female contraceptive, castration of sex offenders.

In a specific embodiment, the method of the invention is for treating and/or preventing hot flashes related to peri-menopausal conditions, menopausal conditions and/or post-menopausal conditions.

In a specific embodiment, the method of the invention is for treating and/or preventing hot flashes which are a consequence of hormone therapy intentionally lowering the level of sex hormones, such as for example therapy-induced hot flashes in breast, uterine or prostate cancers.

The invention further provides a method for lowering and/or suppressing the LH-surge in assisted conception in a patient, comprising administering an effective amount of deuterated fezolinetant or a pharmaceutically acceptable salt or solvate thereof, to a patient in need thereof. Preferably the patient is a warm-blooded animal, more preferably a woman.

The invention further provides a method to cause male castration and to inhibit the sex drive in men, comprising administering an effective amount of deuterated fezolinetant or a pharmaceutically acceptable salt or solvate thereof, to a patient in need thereof. This is of particular interest in the treatment of male sexual offenders.

According to a further feature of the present invention there is provided a method for modulating NK-3 receptor activity, in a patient, preferably a warm-blooded animal, and even more preferably a human, in need of such treatment, which comprises administering to said patient an effective amount of deuterated fezolinetant or a pharmaceutically acceptable salt or solvate thereof.

According to one embodiment, deuterated fezolinetant or a pharmaceutical acceptable salt or solvate may be administered as part of a combination therapy. Thus, are included within the scope of the present invention embodiments comprising coadministration of, and compositions and medicaments which contain, in addition to deuterated fezolinetant, a pharmaceutically acceptable salt or solvate thereof as active ingredient, additional therapeutic agents and/or active ingredients. Such multiple drug regimens, often referred to as "combination therapy", may be used in the treatment and/or prevention of any of the diseases or conditions mediated by or associated with NK-3 receptor modulation. The use of such combinations of therapeutic agents is especially pertinent with respect to the treatment of the above-mentioned disorders within a patient in need of treatment or one at risk of becoming such a patient.

In addition to the requirement of therapeutic efficacy, which may necessitate the use of active agents in addition to the NK-3 receptor modulator deuterated fezolinetant or a pharmaceutical acceptable salt or solvate thereof, there may be additional rationales which compel or highly recommend the use of combinations of drugs involving active ingredients which represent adjunct therapy, i.e., which complement and supplement the function performed by the NK-3 receptor modulator compounds of the present invention. Suitable supplementary therapeutic agents used for the purpose of auxiliary treatment include drugs which, instead of directly treating or preventing a disease or condition mediated by or associated with NK-3 receptor modulation, treat diseases or conditions which directly result from or indirectly accompany the basic or underlying NK-3 receptor modulated disease or condition.

According to a further feature of the present invention, deuterated fezolinetant or a pharmaceutically acceptable salt or solvate thereof may be used in combination therapy with antipsychotic drugs (APD), to improve the efficacy and to minimize secondary effects associated to APD including but not limited to Dopamine 2/3 and 5-HT2 receptors antagonists. More particularly, deuterated fezolinetant or a pharmaceutically acceptable salt or solvate thereof may be used as an adjunct therapy in combination with an atypical antipsychotic drug, including but not limited to risperidone, clozapine, olanzapine, where the NK-3 receptor modulator may serve a role as dose-limiting for the atypical antipsychotic and therefore spare the patient from some of the side effect of those atypical antipsychotic drugs.

Thus, the methods of treatment and pharmaceutical compositions of the present invention may employ deuterated fezolinetant or a pharmaceutical acceptable salt or solvate thereof in the form of monotherapy, but said methods and compositions may also be used in the form of multiple therapy in which deuterated fezolinetant or a pharmaceutically acceptable salt or solvate is coadministered in combination with one or more other therapeutic agents.

In the above-described embodiment combinations of the present invention, deuterated fezolinetant or a pharmaceutically acceptable salt or solvate thereof and other therapeutic active agents may be administered in terms of dosage forms either separately or in conjunction with each other, and in terms of their time of administration, either serially or simultaneously. Thus, the administration of one component agent may be prior to, concurrent with, or subsequent to the administration of the other component agent(s).

The invention also provides pharmaceutical compositions comprising deuterated fezolinetant or a pharmaceutically acceptable salt or solvate thereof and at least one pharmaceutically acceptable carrier, diluent, excipient and/or adjuvant. As indicated above, the invention also covers pharmaceutical compositions which contain, in addition to deuterated fezolinetant or a pharmaceutically acceptable salt or solvate thereof as active ingredient, additional therapeutic agents and/or active ingredients.

Another object of this invention is a medicament comprising at least deuterated fezolinetant a pharmaceutically acceptable salt or solvate thereof, as active ingredient.

According to a further feature of the present invention there is provided the use of deuterated fezolinetant or a pharmaceutically acceptable salt or solvate thereof for the manufacture of a medicament for modulating NK-3 receptor activity in a patient, in need of such treatment, which comprises administering to said patient an effective amount of deuterated fezolinetant or a pharmaceutically acceptable salt or solvate thereof.

As set forth above, deuterated fezolinetant or a pharmaceutically acceptable salt or solvate thereof may be used in monotherapy or in combination therapy. Thus, according to one embodiment, the invention provides the use of deuterated fezolinetant for the manufacture of a medicament for at least one of the purposes described above, wherein said medicament is administered to a patient in need thereof, preferably a warm-blooded animal, and even more preferably a human, in combination with at least one additional therapeutic agent and/or active ingredient. The benefits and advantages of such a multiple drug regimen, possible administration regimens as well as suitable additional therapeutic agents and/or active ingredients are those described above.

Generally, for pharmaceutical use, deuterated fezolinetant may be formulated as a pharmaceutical preparation comprising deuterated fezolinetant and at least one pharmaceutically acceptable carrier, diluent, excipient and/or adjuvant, and optionally one or more further pharmaceutically active compounds.

By means of non-limiting examples, such a formulation may be in a form suitable for oral administration, for parenteral administration (such as by intravenous, intramuscular or subcutaneous injection or intravenous infusion), for topical administration (including ocular), for administration by inhalation, by a skin patch, by an implant, by a suppository, etc. Such suitable administration forms—which may be solid, semi-solid or liquid, depending on the manner of administration—as well as methods and carriers, diluents and excipients for use in the preparation thereof, will be clear to the skilled person; reference is made to the latest edition of Remington's Pharmaceutical Sciences.

Some preferred, but non-limiting examples of such preparations include tablets, pills, powders, lozenges, sachets, cachets, elixirs, suspensions, emulsions, solutions, syrups, aerosols, ointments, cremes, lotions, soft and hard gelatin capsules, suppositories, drops, sterile injectable solutions and sterile packaged powders (which are usually reconstituted prior to use) for administration as a bolus and/or for continuous administration, which may be formulated with carriers, excipients, and diluents that are suitable per se for such formulations, such as lactose, dextrose, sucrose, sorbitol, mannitol, starches, gum acacia, calcium phosphate, alginates, tragacanth, gelatin, calcium silicate, microcrystalline cellulose, polyvinylpyrrolidone, polyethylene glycol, cellulose, (sterile) water, methylcellulose, methyl- and propylhydroxybenzoates, talc, magnesium stearate, edible oils, vegetable oils and mineral oils or suitable mixtures thereof. The formulations can optionally contain other substances that are commonly used in pharmaceutical formulations, such as lubricating agents, wetting agents, emulsifying and suspending agents, dispersing agents, desintegrants, bulking agents, fillers, preserving agents, sweetening agents, flavoring agents, flow regulators, release agents, etc. The compositions may also be formulated so as to provide rapid, sustained or delayed release of the active compound(s) contained therein.

The pharmaceutical preparations of the invention are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 0.05 and 1000 mg, and usually between 1 and 500 mg of deuterated fezolinetant.

Usually, depending on the condition to be prevented or treated and the route of administration, deuterated fezolinetant will usually be administered between 0.001 and 10 mg per kilogram body weight, more often between 0.01 and 4 mg per kilogram body weight of the patient per day, which may be administered as a single daily dose, divided over one or more daily doses, or essentially continuously, e.g. using a drip infusion.

According to one embodiment, deuterated fezolinetant will be administered as a single daily dose, divided over one, two or more daily doses, or essentially continuously, e.g. using a drip infusion.

DEFINITIONS

The definitions and explanations below are for the terms as used throughout the entire application, including both the specification and the claims.

When describing the compounds of the invention, the terms used are to be construed in accordance with the following definitions, unless indicated otherwise.

Bonds from an asymmetric carbon in compounds are generally depicted using a solid line (——), a solid wedge (◢), or a dotted wedge (⦀⦀⦀⦀). The use of either a solid or dotted wedge to depict bonds from an asymmetric carbon atom is meant to indicate that only the stereoisomer shown is meant to be included.

Deuterated fezolinetant contains a stereogenic carbon center at position 8 and thus may exist as (R)- and (S)-enantiomers. Deuterated fezolinetant is the (R)-enantiomer.

In deuterated fezolinetant, the dotted wedge (⦀⦀⦀⦀) carrying the methyl at the C8 position is used to depict the (R)-enantiomer, thus excluding racemic mixtures thereof.

The term "solvate" is used herein to describe deuterated fezolinetant that contains stoichiometric or sub-stoichiometric amounts of one or more pharmaceutically acceptable solvent molecule such as ethanol. The term "hydrate" refers to when the said solvent is water.

All references to deuterated fezolinetant include references to salts, solvates, multi-component complexes and liquid crystals thereof.

All references to deuterated fezolinetant include all polymorphs and crystal habits thereof, prodrugs and prodrugs thereof.

The invention also generally covers all pharmaceutically acceptable predrugs and prodrugs of deuterated fezolinetant.

The invention also generally covers all pharmaceutically acceptable salts of deuterated fezolinetant. Pharmaceutically acceptable salts include the acid addition and base salts thereof. Suitable acid addition salts are formed from acids which form non-toxic salts.

Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine, 2-(diethylamino)ethanol, ethanolamine, morpholine, 4-(2-hydroxyethyl)morpholine and zinc salts. Hemisalts of acids and bases may also be formed, for example, hemisulphate and hemicalcium salts. Preferred, pharmaceutically acceptable salts include hydrochloride/chloride, hydrobromide/bromide, bisulphate/sulphate, nitrate, citrate, and acetate.

The term "patient" refers to a warm-blooded animal, more preferably a human, who/which is awaiting the receipt of, or is receiving medical care or is/will be the object of a medical procedure.

The term "human" refers to a subject of both genders and at any stage of development (i.e. neonate, infant, juvenile, adolescent, adult).

The terms "treat", "treating" and "treatment, as used herein, are meant to include alleviating, attenuating or abrogating a condition or disease and/or its attendant symptoms.

The terms "prevent", "preventing" and "prevention", as used herein, refer to a method of delaying or precluding the onset of a condition or disease and/or its attendant symptoms, barring a patient from acquiring a condition or disease, or reducing a patient's risk of acquiring a condition or disease.

The term "therapeutically effective amount" (or more simply an "effective amount") as used herein means the amount of active agent or active ingredient (e.g. NK-3 antagonist) that is sufficient to achieve the desired therapeutic or prophylactic effect in the patient to which/whom it is administered.

The term "administration", or a variant thereof (e.g. "administering"), means providing the active agent or active ingredient (e.g. a NK-3 antagonist), alone or as part of a pharmaceutically acceptable composition, to the patient in whom/which the condition, symptom, or disease is to be treated or prevented.

By "pharmaceutically acceptable" is meant that the ingredients of a pharmaceutical composition are compatible with each other and not deleterious to the patient thereof.

The term "antagonist" as used herein means a compound that competitively or non-competitively binds to a receptor at the same site as an agonist (for example, the endogenous ligand) and has reversible and competitive binding affinity to a receptor without direct modulation of receptor signaling, but that nonetheless occupies the binding site of an agonist (for example, the endogenous ligand) to thereby block agonist-mediated receptor signaling.

The term "sex hormone-dependent disease" as used herein means a disease which is exacerbated by, or caused by, excessive, inappropriate or unregulated sex hormone production and/or an extraordinary physiological response to sex hormones. Examples of such diseases in men include but are not limited to benign prostatic hyperplasia (BPH), prostatic hyperplasia, metastatic prostatic carcinoma, testicular cancer, androgen dependent acne, male pattern baldness and precocious puberty in boys. Examples of such diseases in women include but are not limited to endometriosis, abnormal puberty, uterine fibrosis, uterine fibroid tumor, uterine leiomyoma, hormone-dependent cancers (ovarian cancer, breast cancer), androgen-producing tumor (virilizing ovarian tumor or virilizing adrenal tumor), hyperandrogenism, hirsutism, virilization, polycystic ovary syndrome (PCOS), premenstrual dysphoric disease (PMDD), HAIR-AN syndrome (hyperandrogenism, insulin resistance and acanthosis *nigricans*), ovarian hyperthecosis (HAIR-AN with hyperplasia of luteinized theca cells in ovarian stroma), other manifestations of high intraovarian androgen concentrations (e.g. follicular maturation arrest, atresia, anovulation, dysmenorrhea, dysfunctional uterine bleeding, infertility), menorrhagia and adenomyosis (abnormal endometrial growth within the muscle of the uterus).

The term "Psychotic disorders" as used herein means a group of illnesses that affect the mind. These illnesses alter a patient's ability to think clearly, make good judgments, respond emotionally, communicate effectively, understand reality, and behave appropriately. When symptoms are severe, patient with psychotic disorders have difficulty staying in touch with reality and are often unable to meet the ordinary demands of daily life. Psychotic disorders include but are not limited to, schizophrenia, schizophreniform disorder, schizo-affective disorder, delusional disorder, brief psychotic disorder, shared psychotic disorder, psychotic disorder due to a general medical condition, substance-induced psychotic disorder or psychotic disorders not otherwise specified (Diagnostic and Statistical Manual of Mental Disorders, Ed. 4th, American Psychiatric Association, Washington, D.C. 1994).

The term "pharmaceutical vehicle" as used herein means a carrier or inert medium used as solvent or diluent in which the pharmaceutically active agent is formulated and/or administered. Non-limiting examples of pharmaceutical vehicles include creams, gels, lotions, solutions, and liposomes.

The present invention will be better understood with reference to the following examples. These examples are intended to representative of specific embodiments of the invention, and are not intended as limiting the scope of the invention.

EXAMPLES

Chemistry Examples

All reported temperatures are expressed in degrees Celsius (° C.); all reactions were carried out at room temperature (rt) unless otherwise stated.

All reactions were followed by thin layer chromatography (TLC) analysis (TLC plates, silica gel 60 $F_{254}$, Merck) was used to monitor reactions, establish silica-gel flash chromatography conditions. All other TLC developing agents/visualization techniques, experimental set-up or purification procedures that were used in this invention, when not described in specific details, are assumed to be known to those conversant in the art and are described in such standard reference manuals as: i) Gordon, A. J.; Ford, R. A. "The Chemist's Companion—A Handbook of Practical Data, Techniques, and References", Wiley: New York, 1972; ii) Vogel's Textbook of Practical Organic Chemistry, Pearson Prentice Hall: London, 1989.

The following abbreviations are used:
CCSC: chlorocarbonylsulfenyl chloride
Cpd: Compound,
DCM: Dichloromethane,
equiv.: Equivalent(s),
EtOH: Ethanol,
g: Gram(s),
h: Hour(s),
mg: Milligram(s),
mL: Milliliter(s),
mmol: Millimole(s),
min: Minute(s),
RT: Room temperature,
$R_t$: retention time
TFA: Trifluoroacetic acid,
TLC: Thin layer chromatography.

The intermediates and compounds described below were named using ChemBioDraw® Ultra version 12.0 (PerkinElmer).

Synthetic Scheme

Deuterated fezolinetant may be synthesized using the methodology described in the following schemes (Part A and Part B):

Part A: Preparation of Deuterated Key Intermediate (ii)

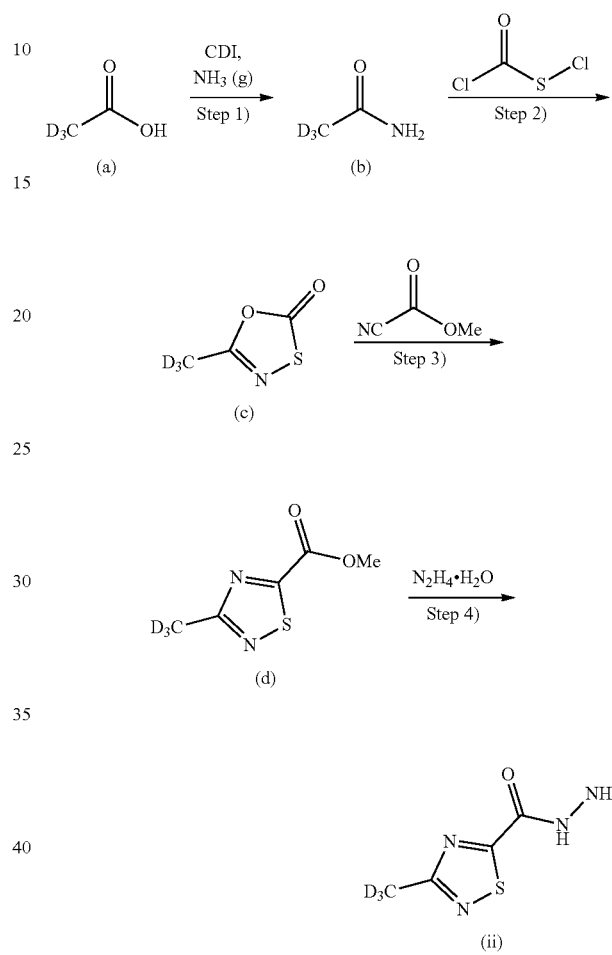

Part B: Synthesis of Deuterated Fezolinetant Using Intermediate (ii)

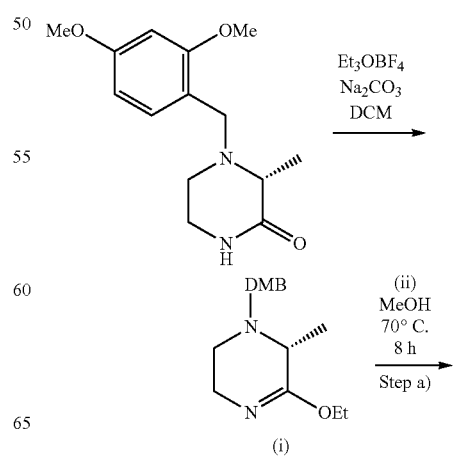

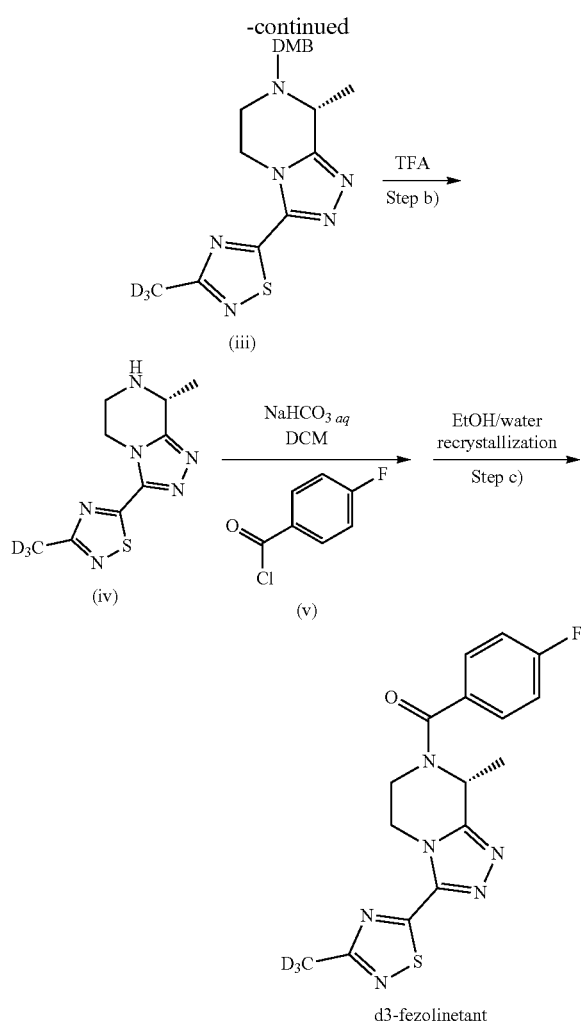

d3-fezolinetant

Synthesis of deuterated fezolinetant was performed through key intermediate (ii). Part A corresponds to the synthesis of intermediate (ii). Part B leads to deuterated fezolinetant (d3-fezolinetant), using intermediate (ii), using procedures adapted from WO2014/154895.

Experimental Details

Part A—Step 1): Formation of $d_3$-Acetamide (b)

To $d_3$-acetic acid (a) (10 g, 1 equiv.) in DCM (100 mL) CDI (25.3 g, 1 equiv.) was added and the resultant mixture stirred at RT for 30 min, thereupon ammonia gas was bubbled through the reaction mixture for 40 min at 0-5° C. Thereafter the bubbling was stopped, the mixture was filtered and the filtrate was evaporated under reduced pressure to give 30.95 g crude product that was purified using flash chromatography on silica to furnish 6.65 g (yield: 73%) deuterated acetamide (b) was obtained (GC (column RTX-1301 30 m×0.32 mm×0.5 μm) $R_t$ 7.4 min, 98%).

Part A—Step 2): Ring Closure Leading to Compound (c)

$d_3$-Acetamide (b) (3.3 g, 1 equiv.) and chlorocarbonylsulfenyl chloride (CCSC) (8.4 g, 1.2 equiv.) were combined in 1,2-dichloroethane (63 mL), and refluxed for 4.5 h. CCSC can be prepared as per the procedure described in Adeppa et al. (Synth. Commun., 2012, Vol. 42, pp. 714-721). The volatiles were then removed to obtain 6.60 g (102% yield) oxathiazolone (c) product as a yellow oil. The product was analyzed by GC ($R_t$=7.8 min, 97%). $^{13}$C NMR (CDCl$_3$): 16.0, 158.7, 174.4 ppm.

Part A—Step 3): Formation of Compound (d)

To oxathiazolone (c) (6.6 g, 1 equiv) in m-xylene (231 mL) methyl cyanoformate (14.70 g, 3.2 equiv.) was added. The mixture was stirred at 130° C. for 19 h and thereafter the volatiles removed under reduced pressure at 50° C. to obtain 4.53 g brown oil (yield: 51%). The product (d) was analyzed by GC($R_t$=11.8 min, 81%) and mass spectrometry (M+H=162).

Part A—Step 4): Formation of Intermediate (ii)

The ester (d) obtained above (3.65 g, 1 equiv.) was dissolved in ethanol (45 mL). The undissolved material was filtered off then hydrazine hydrate (2.3 mL, 1.15 equiv. 55 $^w/_w$ % in H$_2$O) was added to the stirred solution. Thick suspension formed in minutes, the suspension was stirred for 45 min, filtered and washed with EtOH (3 mL) to furnish intermediate (ii) a pale yellow solid (2.43 g, 55% yield). Mass spectrometry (M+H=162, M+Na=184); $^1$H NMR (d$_6$-DMSO): 4.79 ppm (br s, 2H), 10.55 ppm (br s, 1H); $^{13}$C NMR (d$_6$-DMSO): 17.4 ppm, 155.6 ppm, 173.4 ppm, 183.0 ppm.

Part B—Step a): Formation of Compound (iii)

Intermediate (i) was prepared as described in WO2014/154895.

Intermediate (ii) (490 mg, 3.04 mmol) and compound (i) (1.0 g (87 mol % 1.3 content), 2.97 mmol) were taken up in MeOH and the reaction mixture was stirred at a temperature ranging from 55° C. to 70° C. for a period of time ranging from 6 hours to 8 hours. The reaction was deemed complete by TLC. The reaction mixture was evaporated and the crude product was purified by flash chromatography on silica in DCM: MeOH eluent to afford 1.13 g (97% yield) of compound (iii) as a yellow oil. $^1$H NMR (CDCl3): δ (ppm) 7.26 (d, 1H), 6.48-6.49 (2H), 4.50 (m, 1H), 4.30 (m, 1H), 4.09 (m, 1H), 3.94 (d, 1H), 3.80 (s, 6H), 3.61 (d, 1H), 3.22 (m, 1H), 2.75 (m, 1H), 1.72 (d, 3H); Mass spectrometry (M+H=390, 2M+Na=801). Chiral LC (column: Chiralpak IC, 250×4.6 mm—eluent: MTBE/MeOH/DEA 98/2/0.1) 99.84%.

Part B—Step b): Deprotection Leading to Compound (iv)

Intermediate (iii) prepared above (1.05 g, 2.7 mmol) was dissolved in DCM and washed with aq. NaOH. The organic phase was dried, then TFA (1.56 mL, 2.3 g, 7.5 equiv.) was added at RT. The resulting solution was stirred at RT for 2 h. The reaction was monitored by TLC. After completion of the reaction water was added to the reaction mixture, and the precipitate filtered and washed with water. The phases were separated, the pH of the aq. phase was adjusted to pH 13 by addition of 20% aq. NaOH. NaCl was then added to the aqueous solution that was then extracted with DCM. The organic phase was evaporated under reduced pressure to give 504 mg of compound (iv) (78% yield). $^1$H NMR (d$_6$-DMSO): δ (ppm) 4.42 (m, 1H), 4.10 (m, 2H), 3.0 (m, 1H), 2.82 (m, 1H), 1.46 (d, 3H). $^{13}$C NMR (d$_6$-DMSO): δ (ppm) 174.8, 173.4, 156.2, 145.0, 48.1, 45.7, 40.7, 19.1. Mass spectrometry (M+H=240, 2M+Na=501).

Part B—Step c): Acylation and Recrystallization to Form Deuterated Fezolinetant

Intermediate (iv) (450 mg, 1.88 mmol) was dissolved in DCM, then sat. aq. NaHCO$_3$ was added and the mixture was stirred for 30 min. To this mixture 4-fluorobenzoyl chloride (v) (220 μL, 1 equiv.) was added dropwise at RT. The reaction was stirred for a period of time ranging from about 20 min to overnight at RT and reaction progress monitored by TLC. After completion the phases were separated, the organic phase was washed with water, dried over MgSO$_4$, filtered and evaporated under reduced pressure to give 745 mg crude d$_3$-fezolinetant (110% yield). The crude product was purified by flash chromatography using MeOH:DCM together with a second batch, then crystallized (EtOH/H$_2$O) before final analysis. $^1$H NMR (d$_6$-DMSO): δ (ppm) 7.60 (m, 2H), 7.33 (m, 2H), 5.73 (m, 1H), 4.68 (dd, 1H), 4.31 (m, 1H), 4.06 (m, 1H), 3.65 (m, 1H), 1.61 (d, 3H). $^{13}$C NMR (d$_6$-DMSO): δ (ppm) 174.4, 173.5, 168.7, 163.7, 161.8, 154.1, 144.9, 131.6, 129.5, 115.5, 44.7, 18.7. Isotopic purity based on an intense molecular ion observed at m/z=362.2 Da is estimated as approximately 100% isotopic purity. Chiral purity (LC) (column: Chiralpak IC, 250×4.6 mm—eluent: n-hexane/EtOH/DEA 80/20/0.1)>99.9%. A single crystal X-ray structure of the deuterated fezolinetant final product was obtained (FIG. 1) that confirmed the structure of the compound as well as the stereochemistry.

BIOLOGY EXAMPLES

Functional Assay

Aequorin Assay with Human NK-3 Receptor.

Changes in intracellular calcium levels are a recognized indicator of G protein-coupled receptor activity. The efficacy of compounds of the invention to inhibit NKA-mediated NK-3 receptor activation was assessed by an in vitro Aequorin functional assay. Chinese Hamster Ovary recombinant cells expressing the human NK-3 receptor and a construct that encodes the photoprotein apoaequorin were used for this assay. In the presence of the cofactor coelenterazine, apoaequorin emits a measurable luminescence that is proportional to the amount of intracellular (cytoplasmic) free calcium.

Antagonist Testing.

The antagonist activity of compounds of the invention is measured following pre-incubation (3 minutes) of the compound (at various concentrations) with the cells, followed by addition of the reference agonist (NKA) at a final concentration equivalent to the EC$_{80}$ (3 nM) and recording of emitted light (FDSS 6000 Hamamatsu) over the subsequent 90-second period. The intensity of the emitted light is integrated using the reader software. Compound antagonist activity is measured based on the concentration-dependent inhibition of the luminescence response to the addition of Neurokinin A.

Inhibition curves are obtained for compounds of the invention and the concentrations of compounds which inhibit 50% of reference agonist response (IC$_{80}$) were determined (see results in table 1 below). The IC$_{50}$ values shown in table 1 indicate that deuterated fezolinetant is a potent NK-3 antagonist compounds.

Competitive Binding Assays

The affinity of compounds of the invention for the human NK-3 receptor was determined by measuring the ability of compounds of the invention to competitively and reversibly displace a well-characterized NK-3 radioligand in a concentration-dependent manner.

$^3$H-SB222200 Binding Competition Assay with Human NK-3 Receptor.

The ability of compounds of the invention to inhibit the binding of the NK-3 receptor selective antagonist $^3$H-SB222200 was assessed by an in vitro radioligand binding assay. Membranes were prepared from Chinese hamster ovary recombinant cells stably expressing the human NK-3 receptor. The membranes were incubated with 5 nM $^3$H-SB222200 (ARC) in a HEPES 25 mM/NaCl 0.1M/CaCl$_2$ 1 mM/MgCl$_2$ 5 mM/BSA 0.5%/Saponin 10 µg/ml buffer at pH 7.4 and various concentrations of compounds of the invention. The amount of $^3$H-SB222200 bound to the receptor was determined after filtration by the quantification of membrane associated radioactivity using the TopCount-NXT reader (Packard). Competition curves were obtained for compounds of the invention and the concentration that displaced 50% of bound radioligand (IC$_{80}$) were determined by linear regression analysis and then the apparent inhibition constant (K$_i$) values were calculated by the following equation: K$_i$=IC$_{50}$/(1+[L]/K$_d$) where [L] is the concentration of free radioligand and K$_d$ is its dissociation constant at the receptor, derived from saturation binding experiments (Cheng and Prusoff, 1973) (see results in table 1 below).

Table 1 shows biological results obtained using the $^3$H-SB222200 binding competition assay with compounds of the invention. These results indicate deuterated fezolinetant displays potent affinity for the human NK-3 receptor and that deuterated fezolinetant retains the biological activity of fezolinetant.

TABLE 1

| Cpd | Functional assay: Aequorin assay with human NK-3 receptor hNK-3 – AEQ (antagonist IC$_{50}$, nM) | Competitive binding assay with human NK-3 receptor hNK-3 (K$_i$, nM) |
|---|---|---|
| Deuterated fezolinetant | 13 | 17 |
| fezolinetant | 18 | 23 |

CYP 450 Profilling Assay

P450-Glo™ Screening assay (Promega) are used to evaluate the potential of the compounds of the invention to inhibit cytochrome P450 isoforms (CYP 1A2 #V9770, 2C9 #V9790, 2C19 #V9880, 2D6 #V9890, 3A4 #V9910). These assays employ luminogenic CYP450 probe substrates that are derivatives of beetle luciferin, a substrate for luciferase enzymes. The derivatives are converted by P450s cytochrome to luciferin, which in turn reacts with luciferase to produce an amount of light that is directly proportional to the activity of the P450.

P450-Glo™ assays are performed in two steps, the P450-Glo™ substrates are first converted by cytochrome P450 enzyme to a luciferin product which is then detected as a luminescent signal from a luciferase reaction. To perform the assay, the cytochrome P450 mixture with cytochrome P450 enzyme and a P450-Glo™ substrate is prepared at pH 7.4 in a P04 buffer at the optimal concentration for each cytochrome P450 isoform. The compounds of the invention (Dose response curve from 100 µM to 30 nM) are added to the mixture in duplicates. Luciferin-Free water+0.1% DMSO is used as negative control and known inhibitor as positive control. The reactions are initiated by adding the NADPH regeneration system and are performed at 37° C. Luciferin detection reagent is added to stop cytochrome P450 activity and initiate the D-luciferin detection reaction. The IC50 value (compound concentration required to inhibit cytochrome activity by 50%) of the compound of the invention were then determined.

Table 2 shows CYP P450 Inhibition Profile obtained with compound of the invention. When tested in the above-described assay, the deuterated fezolinetant surprisingly displays a better CYP profile on CYP2C9 and 2C19 compare to fezolinetant, indicating no or a very low CYP P450 inhibition on all five Cytochrome P450 isoforms.

TABLE 2

| Cytochrome P450 isoform | Deuterated fezolinetant IC$_{50}$ µM | fezolinetant IC$_{50}$ µM |
|---|---|---|
| CYP1A2 | 100 | 100 |
| CYP2C9 | 100 | 47.95 |
| CYP2C19 | 89.92 | 41.98 |
| CYP2D6 | 100 | 100 |
| CYP3A4 | 92.08 | 90.44 |

Evaluation of Gonadotropins Following Oral Dosing of Deuterated Fezolinetant and Fezolinetant in Castrate Monkey The evaluation of efficacy for agents modulating the hypothalamic-pituitary-gonadal ('HPG') axis may be performed by evaluating luteinizing hormone (LH) in castrate monkeys, as established in the literature (for example, Fraser et al., Endocrinol., 2015, Vol. 156, pp. 4214-4225; Struthers et al., Endocrinol., 207, Vol. 148, pp. 857-867).

Sexually mature, male, cynomolgus monkeys (Macaca fascicularis; N=4, age: 4-5 years, body weight range between 4.41-5.69 kg) were castrated and allowed to recover for >6 months prior to this experiment. Monkeys were group housed and maintained on a 12 h alternating light and dark cycle on a standard laboratory chow diet supplemented with fruit. Water was provided ad libitum. A pilot study was performed where monkeys were treated with vehicle (0.5% methylcellulose/water) and blood samples were collected at the time intervals specified below. This is the response to vehicle. Animals were given a one-week recovery period prior to re-testing, in all cases. The test articles, deuterated fezolinetant and fezolinetant, were similarly formulated in 0.5% methylcellulose/water and administered by oral gavage at 1, 3, and 10 mg/kg (dose volume=5 mL/kg in all cases). Dosing occurred at 08h00. Blood samples were collected by venepuncture at: 0 (pre-dose), 0.5, 1, 1.5, 2.5, 5, 8, 12, 24, 32 and 48 h post-dose. Samples were collected into centrifuge tubes containing K$_2$EDTA and centrifuged at 2500 g for 15 min. The plasma was decanted off the samples into vials designated for pharmacokinetic analysis whereas the serum was collected for LH pharmacokinetic analysis, respectively. All sample vials were immediately frozen and stored at −20° C. until assay.

Serum LH was measured using the Leydig cell method (Wickings et al., J. Reprod. Fert., 1979, Vol. 57, pp. 497-504) according to a method previously qualified with established acceptance criteria for calibration of LH and testosterone. Briefly, for each run, 2-3 male mice were sacrificed, testes collected and a Leydig cell suspension prepared according to published methods. Treatment of Leydig cells with LH will elicit the secretion of testosterone and the latter is measured by ELISA. For each run, a standard (monkey LH standards, Scripps) curve for LH was constructed by plotting the log (LH concentration) against the square root of the testosterone produced, which gave a linear plot over the dose range. The formula of this standard curve was then used for the quantification of LH concentration in unknown samples (eg. collected from the in vivo testing) by interpolation.

Pharmacokinetic (PK) analyses were performed on plasma samples collected at coincident time intervals as for the LH analyses. Liquid chromatography coupled with tandem mass spectrometry method (LC-MS/MS) was established to quantify fezolinetant and deuterated fezolinetant concentrations in cynomolgus monkey plasma samples (determinations validated by comparison against an internal standard). PK parameters were calculated using non-compartmental analysis (Phoenix™ WinNonlin, version 6.1). The linear log trapezoidal algorithm, weighting 1/Y*Y was used for parameters calculation. Mean PK parameters were calculated from individual animals in each treatment group. Concentrations below the lower limit of quantification (LLOQ) were excluded for the calculation of PK parameters.

The invention claimed is:

1. (R)-(4-fluorophenyl)-(8-methyl-3-(3-(methyl-d3)-1,2, 4-thiadiazol-5-yl)-5,6-dihydro-[1,2,4]trizolol[4,3-a]pyrazin-7(8H)-yl)methanone or a pharmaceutically acceptable salt or solvate thereof.

2. The (R)-(4-fluorophenyl)-(8-methyl-3-(3-(methyl-d3)-1,2,4-thiadiazol-5-yl)-5,6-dihydro-[1,2,4]trizolo[4,3-a]pyrazin-7(8H)-yl)methanone or a pharmaceutically acceptable salt or solvate thereof according to claim 1, formulated in a pharmaceutical composition comprising at least one pharmaceutically acceptable carrier, diluent, excipient and/or adjuvant.

3. A method for modulating NK-3 receptor activity in a patient, comprising administering to a patient in need thereof a therapeutically effective amount of (R)-(4-fluorophenyl)-(8-methyl-3-(3-(methyl-d3)-1,2,4-thiadiazol-5-yl)-5,6-dihydro-[1,2,4]trizolo[4,3-a]pyrazin-7(8H)-yl)methanone or a pharmaceutically acceptable salt or solvate thereof.

4. The method according to claim 3, for treating a disease selected from depression, anxiety, psychosis, schizophrenia, psychotic disorders, bipolar disorders, cognitive disorders, Parkinson's disease, Alzheimer's disease, attention deficit hyperactivity disorder (ADHD), pain, convulsion, obesity, inflammatory diseases including irritable bowel syndrome (IBS) and inflammatory bowel disorders, emesis, preeclampsia, airway related diseases including chronic obstructive pulmonary disease, asthma, airway hyperresponsiveness, bronchoconstriction and cough, urinary incontinence, reproduction disorders, contraception and sex hormone-dependent diseases, benign prostatic hyperplasia (BPH), prostatic hyperplasia, metastatic prostatic carcinoma, testicular cancer, breast cancer, ovarian cancer, androgen dependent acne, male pattern baldness, endometriosis, abnormal puberty, uterine fibrosis, uterine fibroid tumor, uterine leiomyoma, hormone-dependent cancers, hyperandrogenism, hirsutism, virilization, polycystic ovary syndrome (PCOS), premenstrual dysphoric disease (PMDD), HAIR-AN syndrome (hyperandrogenism, insulin resistance and acanthosis nigricans), ovarian hyperthecosis (HAIR-AN with hyperplasia of luteinized theca cells in ovarian stroma), other manifestations of high intraovarian androgen concentrations, follicular maturation arrest, atresia, anovulation, dysmenorrhea, dysfunctional uterine bleeding, infertility, androgen-producing tumor (virilizing ovarian tumor or virilizing adrenal tumor), menorrhagia and adenomyosis.

5. The method according to claim 3, for treating hot flashes.

6. The method according to claim 3, for lowering the circulating LH levels.

7. A process of manufacturing (R)-(4-fluorophenyl)-(8-methyl-3-(3-(methyl-d3)-1,2,4-thiadiazol-5-yl)-5,6-dihydro-[1,2,4]trizolo[4,3-a]pyrazin-7(8H)-yl)methanone or a pharmaceutically acceptable salt or solvate thereof, comprising the steps of:

a) reacting a compound of Formula (i)

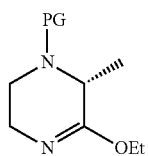
(i)

wherein:
PG represents a suitable protecting group;
with a compound of Formula (ii)

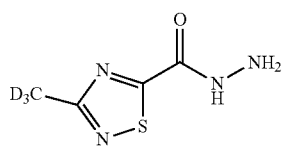
(ii)

so as to obtain a compound of Formula (iii)

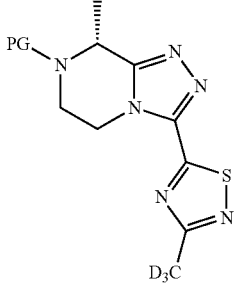
(iii)

wherein PG is as defined above;
b) deprotecting compound of Formula (iii) with a suitable deprotection agent to afford compound of Formula (iv)

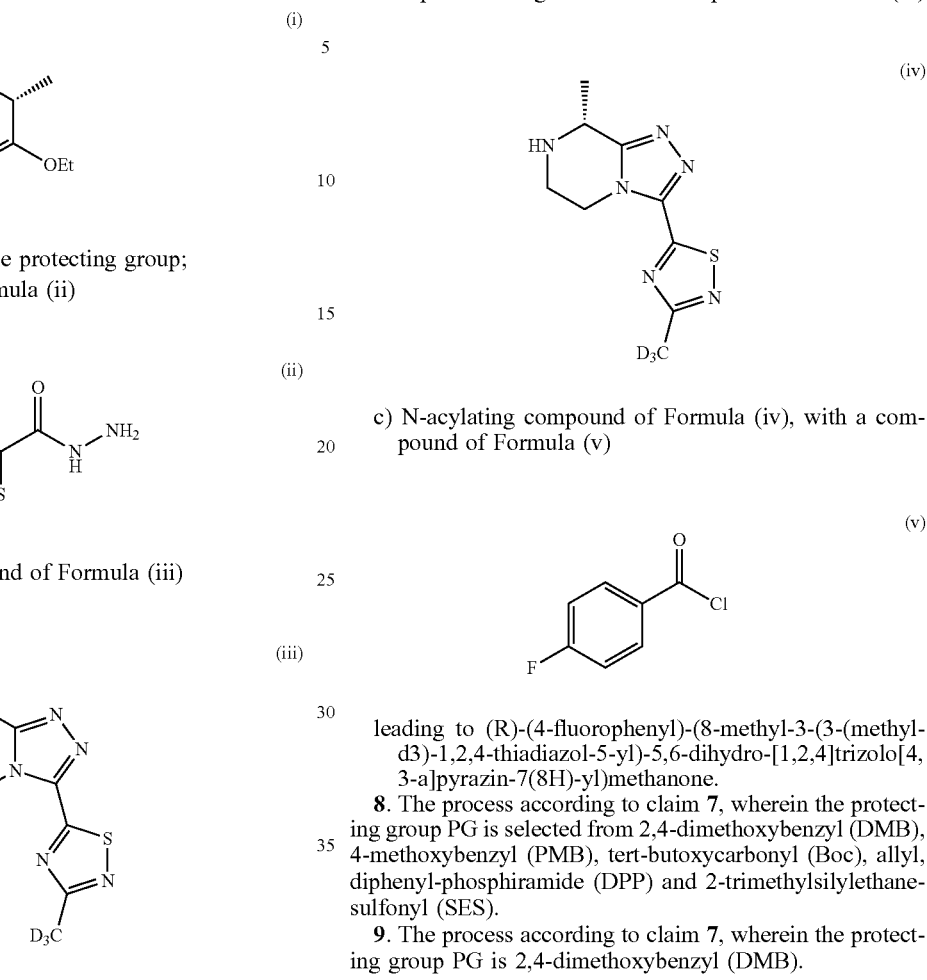
(iv)

c) N-acylating compound of Formula (iv), with a compound of Formula (v)

(v)

leading to (R)-(4-fluorophenyl)-(8-methyl-3-(3-(methyl-d3)-1,2,4-thiadiazol-5-yl)-5,6-dihydro-[1,2,4]trizolo[4,3-a]pyrazin-7(8H)-yl)methanone.

8. The process according to claim 7, wherein the protecting group PG is selected from 2,4-dimethoxybenzyl (DMB), 4-methoxybenzyl (PMB), tert-butoxycarbonyl (Boc), allyl, diphenyl-phosphiramide (DPP) and 2-trimethylsilylethane-sulfonyl (SES).

9. The process according to claim 7, wherein the protecting group PG is 2,4-dimethoxybenzyl (DMB).

\* \* \* \* \*